United States Patent
Houser et al.

(10) Patent No.: US 9,675,375 B2
(45) Date of Patent: Jun. 13, 2017

(54) ULTRASONIC SURGICAL SYSTEM AND METHOD

(75) Inventors: Kevin L. Houser, Springboro, OH (US); William T. Donofrio, Andover, MN (US); Foster B. Stulen, Mason, OH (US)

(73) Assignee: ETHICON LLC, Guaynabo, PR (US)

( * ) Notice: Subject to any disclaimer, the term of this patent is extended or adjusted under 35 U.S.C. 154(b) by 1329 days.

(21) Appl. No.: 11/392,040

(22) Filed: Mar. 29, 2006

(65) Prior Publication Data
US 2007/0239028 A1     Oct. 11, 2007

(51) Int. Cl.
*A61B 17/32*     (2006.01)
*A61B 34/32*     (2016.01)
(Continued)

(52) U.S. Cl.
CPC ...... *A61B 17/320092* (2013.01); *A61B 34/30* (2016.02); *A61B 34/32* (2016.02); *A61B 34/37* (2016.02); *A61B 34/70* (2016.02); *A61B 34/71* (2016.02); *A61B 2017/00022* (2013.01); *A61B 2017/00026* (2013.01); *A61B 2017/00084* (2013.01)

(58) Field of Classification Search
USPC ........ 606/130, 38, 169, 1, 28; 600/109, 118, 600/429; 700/245, 246, 264, 258, 260; 901/31, 32, 39; 604/22
See application file for complete search history.

(56) References Cited

U.S. PATENT DOCUMENTS 4,486,928 A * 12/1984 Tucker et al. ............... 29/26 A
4,827,911 A *  5/1989 Broadwin et al. ............ 601/4
(Continued)

FOREIGN PATENT DOCUMENTS

JP     01-171537     7/1989
JP     05-095955     4/1993
(Continued)

OTHER PUBLICATIONS

JP, Notification of Reasons for Refusal, Japanese Application No. 2007-085223 (Mar. 13, 2012).
(Continued)

*Primary Examiner* — Jocelin Tanner
(74) *Attorney, Agent, or Firm* — Thompson Hine LLP

(57) ABSTRACT

An ultrasonic surgical system has an ultrasonic unit including an instrument operatively connected to an ultrasonic generator, wherein the instrument has an ultrasonic end effector on the distal end of a shaft. The system further includes a positioning unit including a movable arm adapted for releasably holding the instrument, whereby an operator may direct the positioning unit to position the end effector at a surgical site inside a body cavity of a patient for performing a plurality of surgical tasks. The system further includes a control unit operatively connected to the ultrasonic and positioning units, wherein the control unit is programmable with a surgical subroutine for performing the surgical tasks. The system further includes a user interface operatively connected to the control unit for initiating an operative cycle of the surgical subroutine such that the surgical tasks are automatically performed during the operative cycle.

19 Claims, 10 Drawing Sheets

(51) Int. Cl.
*A61B 34/00* (2016.01)
*A61B 34/30* (2016.01)
*A61B 34/37* (2016.01)
*A61B 17/00* (2006.01)

(56) References Cited

U.S. PATENT DOCUMENTS

| | | | |
|---|---|---|---|
| 5,322,055 | A | 6/1994 | Davison et al. |
| 5,449,370 | A * | 9/1995 | Vaitekunas ............... 606/169 |
| 5,464,013 | A * | 11/1995 | Lemelson ................ 600/427 |
| 5,607,433 | A * | 3/1997 | Polla et al. .............. 606/107 |
| 5,817,119 | A * | 10/1998 | Klieman et al. .......... 606/174 |
| 5,893,835 | A * | 4/1999 | Witt et al. ................ 601/2 |
| 5,954,736 | A | 9/1999 | Bishop et al. |
| 5,997,528 | A * | 12/1999 | Bisch et al. .............. 606/1 |
| 6,056,735 | A * | 5/2000 | Okada et al. ............. 606/1 |
| 6,241,703 | B1 | 6/2001 | Levin et al. |
| 6,277,084 | B1 | 8/2001 | Abele et al. |
| 6,309,397 | B1 | 10/2001 | Julian et al. |
| 6,325,808 | B1 | 12/2001 | Bernard et al. |
| 6,352,532 | B1 * | 3/2002 | Kramer et al. ............ 606/41 |
| 6,450,975 | B1 | 9/2002 | Brennan et al. |
| 6,454,781 | B1 * | 9/2002 | Witt et al. ................ 606/169 |
| 6,589,253 | B1 | 7/2003 | Cornish et al. |
| 6,679,879 | B2 * | 1/2004 | Shadduck ................ 606/41 |
| 6,773,409 | B2 * | 8/2004 | Truckai et al. ........... 601/2 |
| 6,773,444 | B2 | 8/2004 | Messerly |
| 6,783,524 | B2 | 8/2004 | Anderson et al. |
| 6,786,896 | B1 | 9/2004 | Madhani et al. |
| 6,850,817 | B1 | 2/2005 | Green |
| 2001/0014801 | A1 * | 8/2001 | Tovey et al. ............. 606/1 |
| 2001/0025183 | A1 * | 9/2001 | Shahidi ................... 606/130 |
| 2002/0177843 | A1 * | 11/2002 | Anderson et al. ........ 606/1 |
| 2004/0127926 | A1 | 7/2004 | Beaupre |
| 2004/0167496 | A1 | 8/2004 | Poole et al. |
| 2004/0176686 | A1 | 9/2004 | Hare et al. |
| 2004/0176751 | A1 | 9/2004 | Weitzner et al. |
| 2005/0256522 | A1 * | 11/2005 | Francischelli et al. ..... 606/41 |
| 2006/0278680 | A1 * | 12/2006 | Viola et al. .............. 227/176.1 |
| 2007/0078484 | A1 * | 4/2007 | Talarico et al. ........... 606/205 |

FOREIGN PATENT DOCUMENTS

| | | |
|---|---|---|
| JP | 06-114069 | 4/1994 |
| JP | 07-136173 | 5/1995 |
| JP | 11-178834 | 7/1999 |
| JP | 11-192233 | 7/1999 |
| JP | 2002-085420 | 3/2002 |
| JP | 2004-208922 | 7/2004 |
| WO | 03/030754 | 4/2003 |
| WO | 2004/058074 | 7/2004 |
| WO | 2006/020943 | 2/2006 |

OTHER PUBLICATIONS

CN, First Office Action, Chinese Application No. 200710101631.2 (Jan. 15, 2010).

CN, Second Office Action, Chinese Application No. 200710101631.2 (Jul. 5, 2010).

AU, Office Action, Australian Application No. 2007201266 (Feb. 23, 2012).

EP, Search Report, European Application No. 07251342.7 (Jul. 24, 2007).

JP, Notification of Reasons for Refusal, Japanese Application No. 2007-085223 (Jan. 31, 2013).

IN, First Examination Report, Indian Application No. 492/KOL/2007, 2 pages, Feb. 25, 2015.

* cited by examiner

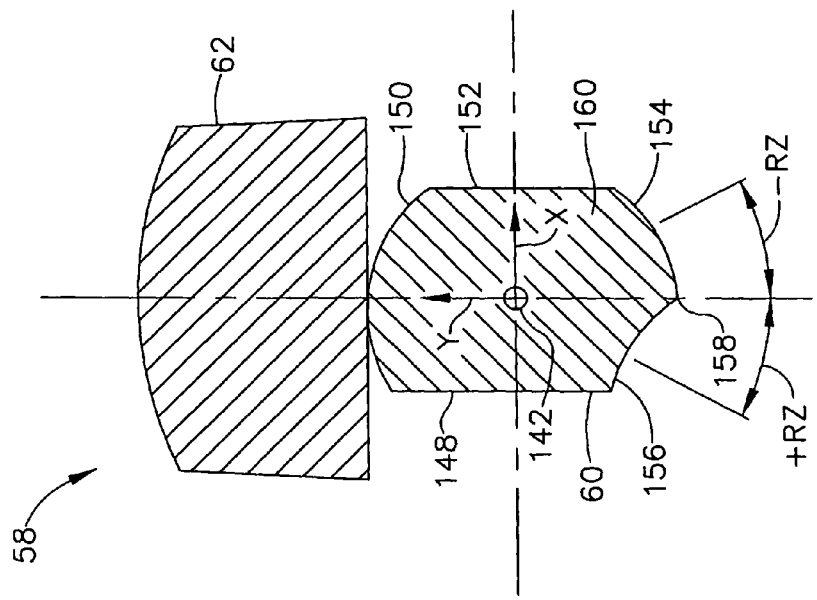
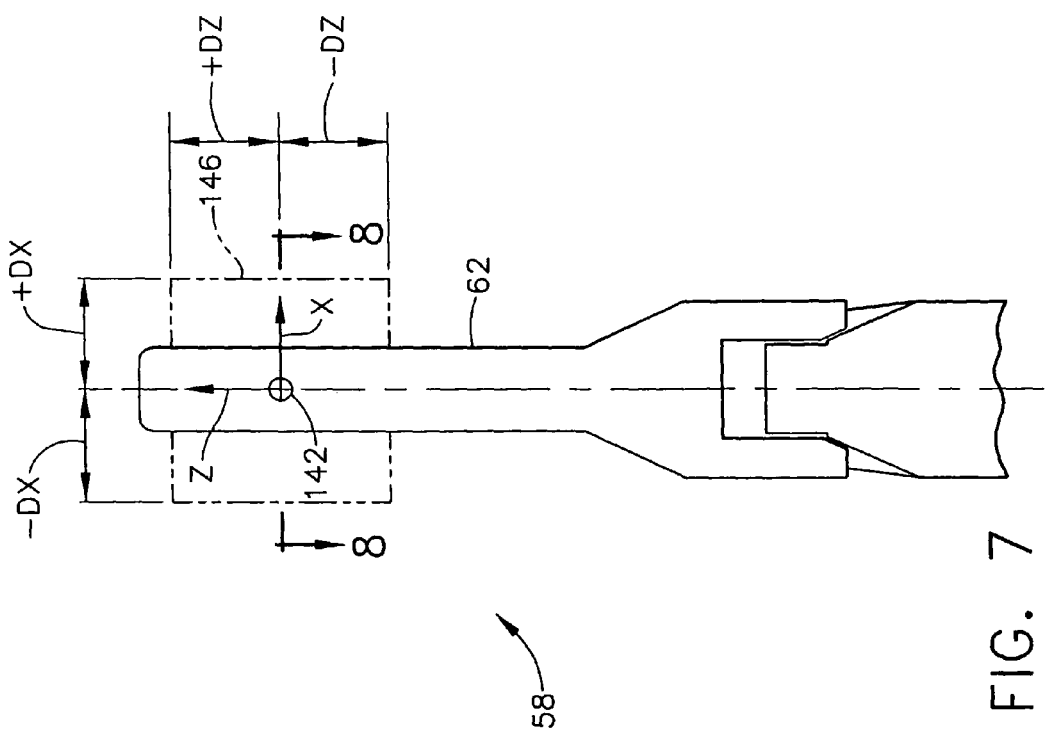
FIG. 8
FIG. 7

U/S POWER

JAW ANGLE, A

LATERAL POSITION, DX

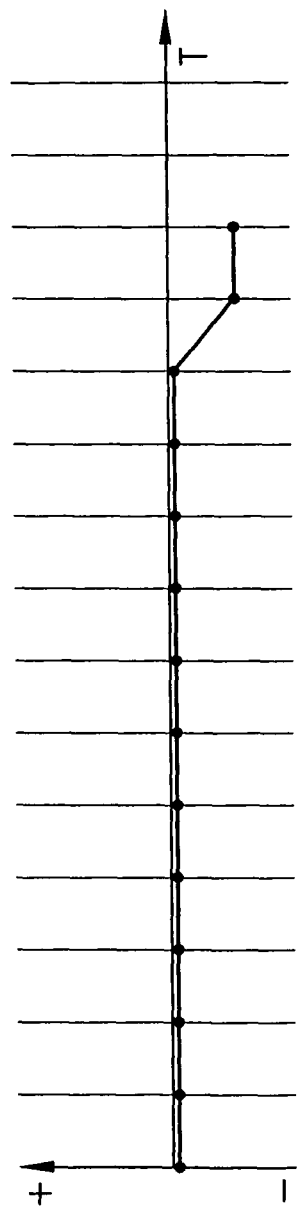
FIG. 12 — LONGITUDINAL POSITION, DZ
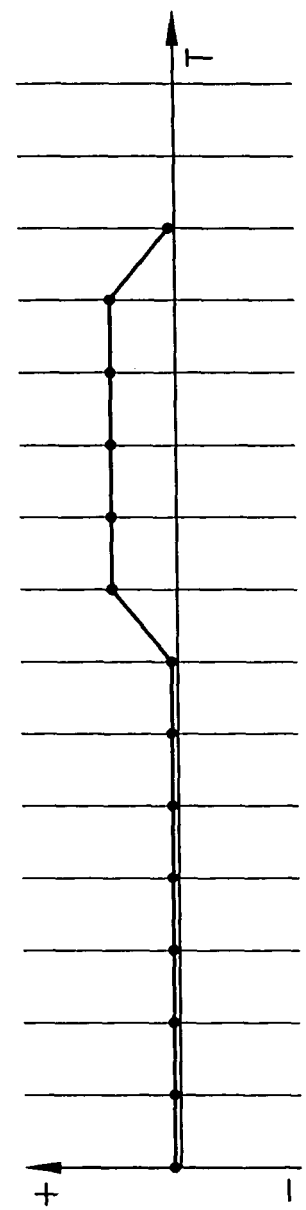
FIG. 13 — BLADE ROTATION, RZ

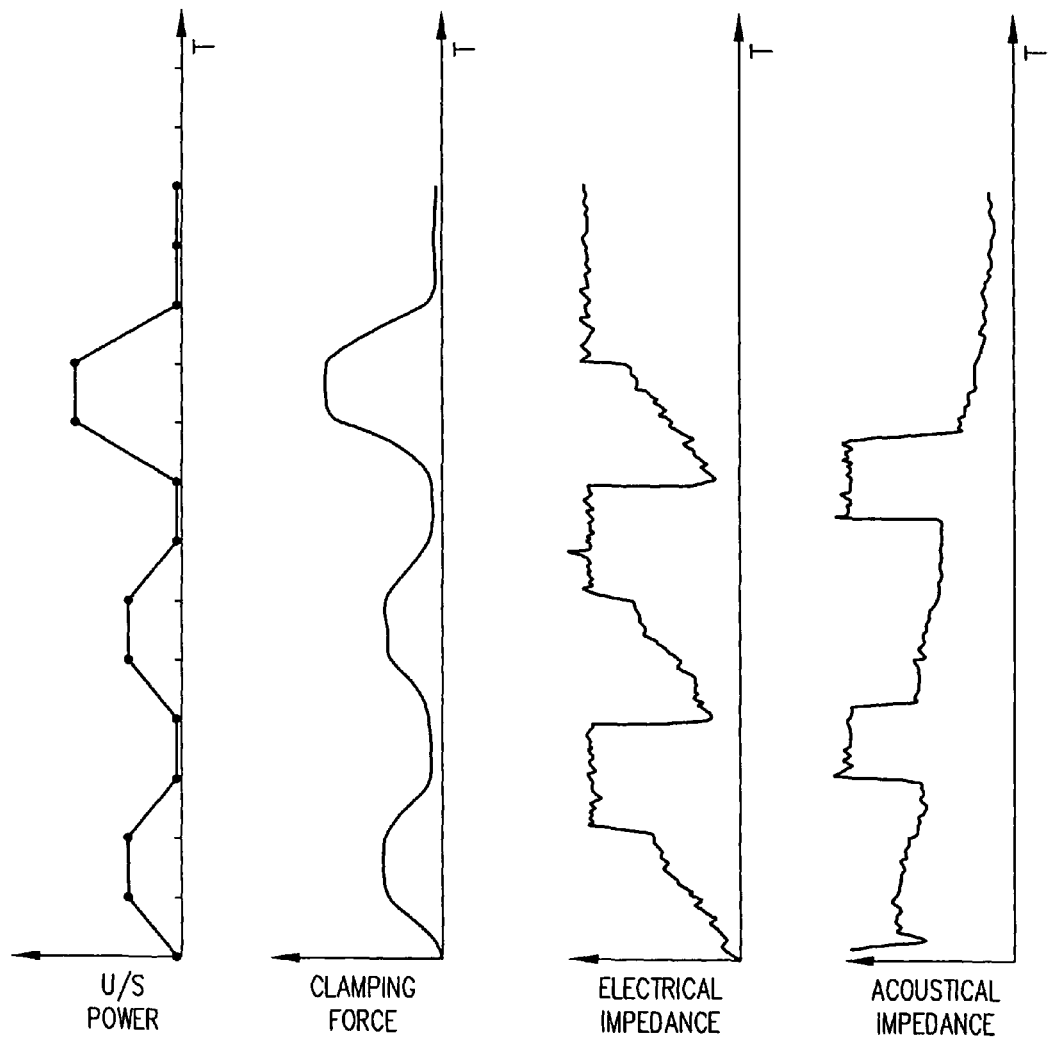

ULTRASONIC SURGICAL SYSTEM AND METHOD

FIELD OF THE INVENTION

The present application relates to ultrasonic surgical instruments and, more particularly, to ultrasonic surgical instruments having end effectors for cutting and coagulating tissue. The present application also relates to robotic surgical systems and, more particularly, to robotic surgical systems used with ultrasonic surgical instruments.

BACKGROUND OF THE INVENTION

Surgeons use ultrasonic instruments in surgery to cut and coagulate tissue. Piezoelectric elements are electrically excited at a resonant frequency of an ultrasonic instrument to create vibrations that are transmitted through a resonator and amplified to produce a mechanical, standing wave vibration of the same frequency. An ultrasonic transmission assembly of the instrument has an elongated, transmission waveguide that transmits this vibration to an end effector (e.g., cutting blade) on the distal tip of the instrument. An example of an ultrasonic surgical instrument is the Harmonic Scalpel® Laparosonic® Coagulating Shears, available from Ethicon Endo-Surgery, Inc., Cincinnati, Ohio.

In recent years, minimally invasive robotic systems have been developed and used for certain surgical procedures including coronary artery bypass grafting and cholecystectomy procedures. The robotic systems provide a number of promising benefits that generally reduce the surgical skill required to perform certain surgical procedures, such as by increasing dexterity and eliminating hand tremor. The robotic systems also allow surgeons to perform the procedures at a remote location, wherein remote may be understood as anywhere that is "more than arm's length" from the patient. An example of a robotic surgical system is the DA VINCI, which is available from Intuitive Surgical Inc., Mountain View, Calif.

U.S. Pat. No. 6,783,524 to Anderson et al. titled "Robotic Surgical Tool with Ultrasound Cauterizing and Cutting Instrument" discloses an ultrasonic surgical instrument mounted to a movable arm of a robotic surgical system such as the DA VINCI. The disclosed method for enhancing robotic surgery generally includes coupling the instrument to the robotic surgical system, positioning an end effector of the instrument in contact with tissue at a surgical site and delivering ultrasound energy to the tissue. In general, the disclosed robotic system permits a surgeon to directly control the movements and actuation of the instrument from a remote location.

Despite such advances in surgical technologies, however, considerable skill is still required by surgeons to perform particular steps of some surgical procedures. For example, in order to ultrasonically coagulate a vessel such as the cystic duct of the gall bladder, the surgeon may press a relatively broad surface of the ultrasonic blade against the duct, apply a light clamping force on the duct and sweep the ultrasonic end effector within a treatment region on the duct while applying an intermediate level of ultrasonic power. Then, to cut the duct, the surgeon may present an edge of the blade to the duct, apply a high clamping force on the duct while holding the blade stationary and apply a high level of ultrasonic power. The surgeon may repeat these steps several times during a surgical procedure on a patient.

In order to reduce the time to perform certain surgical procedures and to improve surgical outcomes, surgeons would like to employ various techniques that are not normally practical using current surgical systems. For example, many surgeons would like to have a way to apply a rapidly pulsed clamping force onto tissue while applying ultrasonic energy in order to agitate and/or circulate fluids in the tissue to quicken fluid dessication, thereby shortening the time to coagulate the tissue. Surgeons also would like to have a way to consistently apply the correct power level of ultrasonic energy for the correct duration, primarily in order to avoid injury such as lateral thermal damage to the tissue, but also to quicken the procedure while having the assurance that the tissue seal is hemostatic. Surgeons rely greatly on their physical senses to estimate clamping force on the tissue and the power level/duration of ultrasonic energy that should be applied to the tissue. Obviously, some of this sensory feedback is greatly diminished if the surgeon is using a robotic surgical system and separated from the patient.

Clearly, it may be very difficult, if not impossible, for a surgeon to perform a plurality of surgical tasks in a well-coordinated manner, wherein the tasks may include, for example, sweeping the ultrasonic blade on tissue, rotating the blade, pulsing the clamping force and applying ultrasonic energy at various power levels.

Accordingly, there is a need for an ultrasonic surgical system and method of ultrasonically treating tissue of a patient during a surgical procedure, wherein certain surgical tasks may be automatically and consistently performed, thereby reducing the skill level required by the surgeon to perform the tasks, improving the surgical outcome, reducing the surgical procedure time and further improving the ability to perform surgical procedures remotely.

SUMMARY OF THE INVENTION

In one aspect, an ultrasonic surgical system has an ultrasonic unit including an instrument operatively connected to an ultrasonic generator, wherein the instrument has an ultrasonic end effector on the distal end of a shaft. The system further includes a positioning unit including a movable arm adapted for releasably holding the instrument, whereby an operator may direct the positioning unit to position the end effector at a surgical site inside a body cavity of a patient for performing a plurality of surgical tasks. The system further includes a control unit operatively connected to the ultrasonic and positioning units, wherein the control unit is programmable with a surgical subroutine for performing the surgical tasks. The system further includes a user interface operatively connected to the control unit for initiating an operative cycle of the surgical subroutine such that the surgical tasks are automatically performed during the operative cycle.

In another aspect, a method for ultrasonically treating the tissue of a surgical patient includes providing the ultrasonic surgical system defined in the previous paragraph, programming the control unit with a surgical subroutine for performing a plurality of surgical tasks, positioning the end effector of the instrument at a surgical site inside a body cavity of the patient and initiating the surgical subroutine of the control unit, whereby the system automatically performs the surgical tasks according to the surgical subroutine.

In another aspect, a method for ultrasonically treating the tissue of a surgical patient includes providing the ultrasonic surgical system defined in the previous aspects and further including a feedback system having at least one sensor positioned in at least one of the ultrasonic and positioning units and having an associated sensor circuit, wherein the feedback system is operatively connected to the control unit, and wherein a feedback signal associated with an operational performance parameter of the instrument during the operative cycle may be transmitted from the sensor to the control unit such that the control system can process the feedback signal and respond according to the surgical subroutine. The method further includes programming the control unit with a surgical subroutine for performing a plurality of surgical tasks, positioning the end effector of the instrument at a surgical site inside a body cavity of the patient and initiating the surgical subroutine of the control unit, whereby the system automatically performs the surgical tasks, processes the feedback signal and responds to the feedback signal according to the surgical subroutine.

A third embodiment of the invention is for an energy-based medical treatment system including an energy-based clamp coagulator having two clamping members adapted to coagulate patient tissue clamped between the two clamping members, wherein at least one of the two clamping members includes, or is adapted to function as, a temperature sensor for measuring a temperature of the clamped patient tissue.

Other aspects and aspects of the ultrasonic surgical system and method of ultrasonically cutting and coagulating tissue of a patient during a surgical procedure will become apparent from the following description, the accompanying drawings, and the appended claims.

BRIEF DESCRIPTION OF THE FIGURES

FIG. 7 is a top view of the distal portion of the instrument shown in FIG. 4;

FIG. 8 is cross-sectional view, taken at line 8-8 of FIG. 7, of the instrument shown in FIG. 4;

FIG. 12 is a graph depicting a longitudinal position of the end effector versus time during the operative cycle in accordance with one aspect of the ultrasonic surgical system;

FIG. 13 is a graph depicting a rotational position of a blade of the end effector versus time during the operative cycle in accordance with one aspect of the ultrasonic surgical system;

FIG. 14 is a graph depicting the ultrasonic power applied to the end effector versus time during the operative cycle in accordance with one aspect of the ultrasonic surgical system and is the same graph as shown in FIG. 9;

FIG. 15 is a graph depicting a measured clamping force feedback of the end effector on tissue versus time during the operative cycle in accordance with one aspect of the ultrasonic surgical system;

FIG. 16 is a graph depicting a measured electrical impedance feedback versus time during the operative cycle in accordance with one aspect of the ultrasonic surgical system; and FIG. 17 is a graph depicting a measured acoustical impedance feedback versus time during the operative cycle in accordance with one aspect of the ultrasonic surgical system.

DETAILED DESCRIPTION OF THE INVENTION

The following description pertains to an ultrasonic surgical system and method for performing a surgical procedure according to an automated surgical subroutine. The system and method may be particularly useful for ultrasonically cutting and coagulating soft tissue in a patient, but the system and method may also be adapted to other types of surgical procedures. A surgeon may initiate the surgical subroutine during a surgical procedure to perform a plurality of surgical tasks simultaneously and/or in a coordinated manner, wherein the surgical tasks may include sweeping an ultrasonic blade of the instrument against the tissue, rotating the blade, actuating a clamping element, applying various power levels of ultrasonic energy and obtaining feedback signals associated with the performance of the instrument.

Figure 1:
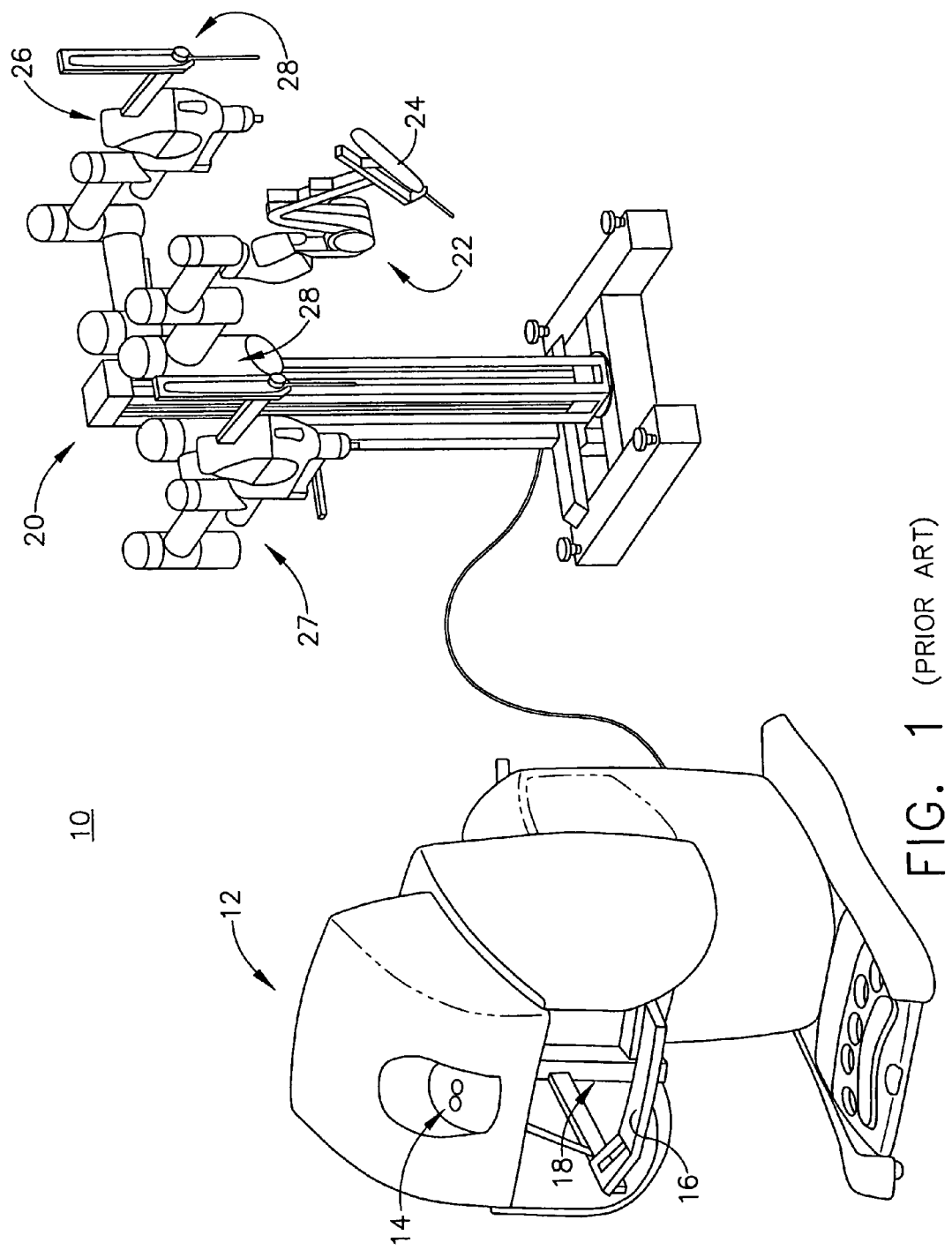
FIG. 1 is a perspective view of a robotic surgical apparatus of the prior art.

The ultrasonic surgical system to be described herein may include or be used in conjunction with a surgical robotic apparatus such as the prior art DA VINCI system (Intuitive Surgical, Inc.) shown in FIG. 1. The robotic apparatus, generally designated 10, is disclosed in the earlier referenced U.S. Pat. No. 6,783,524, the entire contents of which are incorporated herein by reference. Robotic apparatus 10 includes a control station 12 and a surgical work station 20. Control station 12 includes an image display module 14 for displaying an image of a surgical site, a support 16 on which an operator may rest his/her forearms and a space 18 where two master control devices are located (not shown). When using control station 12, a surgeon may sit in a chair in front of control station 12, view the surgical site through display module 14 and grip the master controls, one in each hand, while resting the forearms on support 16.

Control station 12 is generally coupled to work station 20 such that command from the master control devices may be transmitted to work station 20. Work station 20 is mobile and may be positioned adjacent to a surgical patient. Control station 12 may be positioned a great distance from work station 20, but typically control station 12 is positioned in the same operating room as work station 20.

According to various aspects, work station 20 may include at least three robotic arm assemblies 22, 26, 27 (also referred to as movable arms), one of which may be configured to hold an image capture device 24 and the others of which may be configured to hold surgical instruments 28. Coupling of work station 20 to control station 12 generally enables display module 14 to display an image captured by image capture device 24 and control of movable arms 22, 26, 27.

Surgical instruments 28 typically include an elongate shaft for endoscopic access to the surgical site inside the patient, wherein the shaft has a distal end effector adapted for a particular surgical task. Instruments 28 may be releasably mounted on wrist-like mechanisms on movable arms 22, 26, 27 such that a surgeon may use control station 12 to move each instrument 28 in various directions (i.e., arms 22, 26, 27 have a plurality of degrees of freedom).

Figure 2:
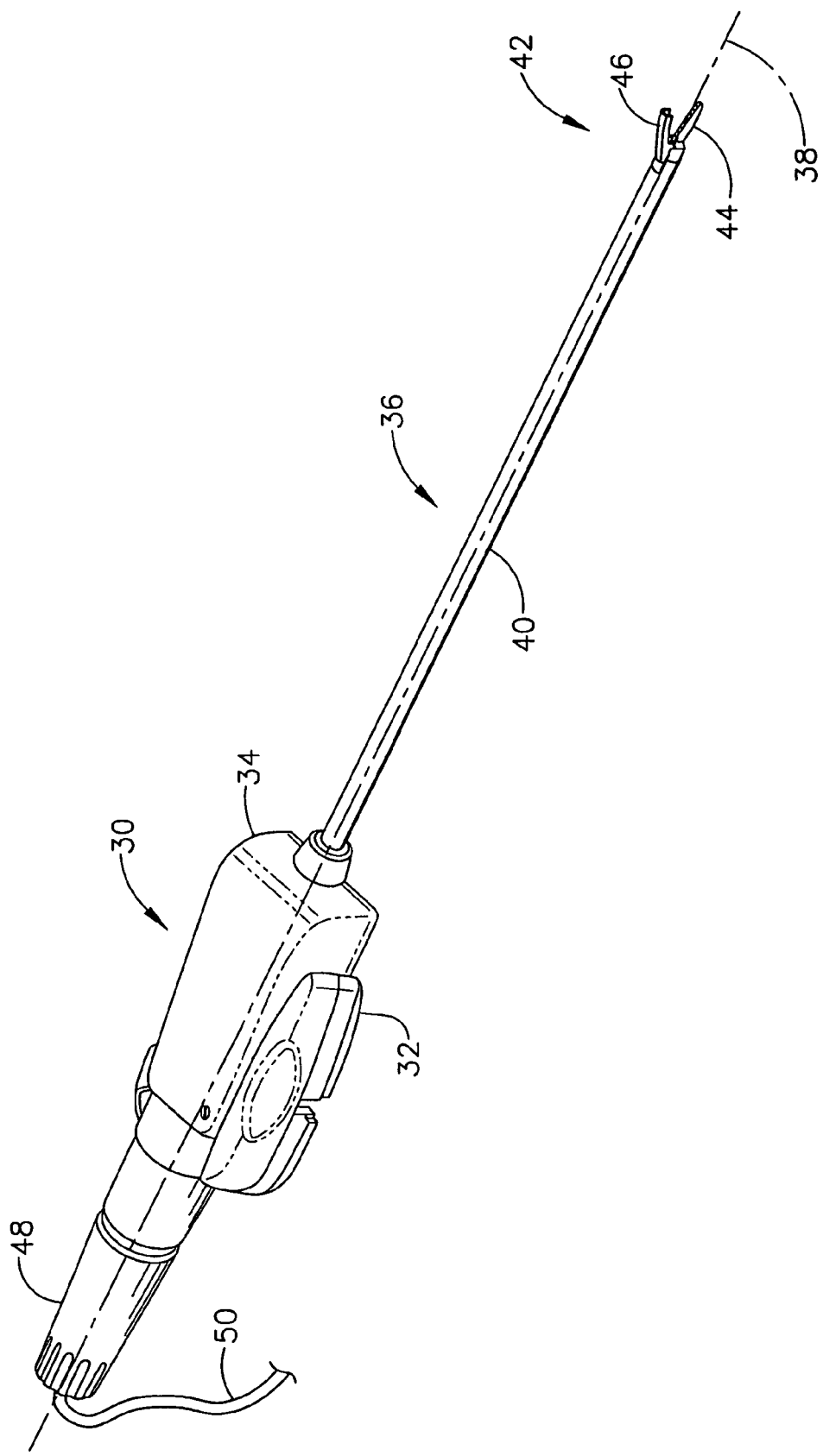
FIG. 2 is a perspective view of an ultrasonic surgical tool of the prior art for use on the robotic surgical apparatus shown in FIG. 1.

FIG. 2 is a perspective view of an alternative aspect of surgical instrument 28 shown in FIG. 1 and is described in detail in U.S. Pat. No. 6,783,524. This aspect, generally designated 30, includes an instrument base 32 having a cover 34. Instrument 30 also includes a shaft 36 extending distally from instrument base 32 along the instrument axis 38. Shaft 36 includes an outer sheath 40. An end effector 42 couples to the distal end of shaft 36 and includes an ultrasonic blade 44 that cooperatively mates with a clamp 46. An ultrasonic transducer 48 mounts to the proximal end of base 32 and a power/control cable 50 may be operatively connected to a conventional ultrasonic surgical generator, such as the Auto Sonix™ generator (not shown) made by United States Surgical Corporation of Norwalk, Conn.

While seated at the control station, a surgeon may introduce and position the distal portion of instrument 30 into a body cavity of a patient and manipulate and ultrasonically treat tissues therein. While seated at control station 12 of robotic apparatus 10, the surgeon may steer end effector 42 to the surgical site inside the patient, actuate end effector 42 to clamp onto tissue and energize blade 44 to cut and coagulate tissue.

Figure 3:
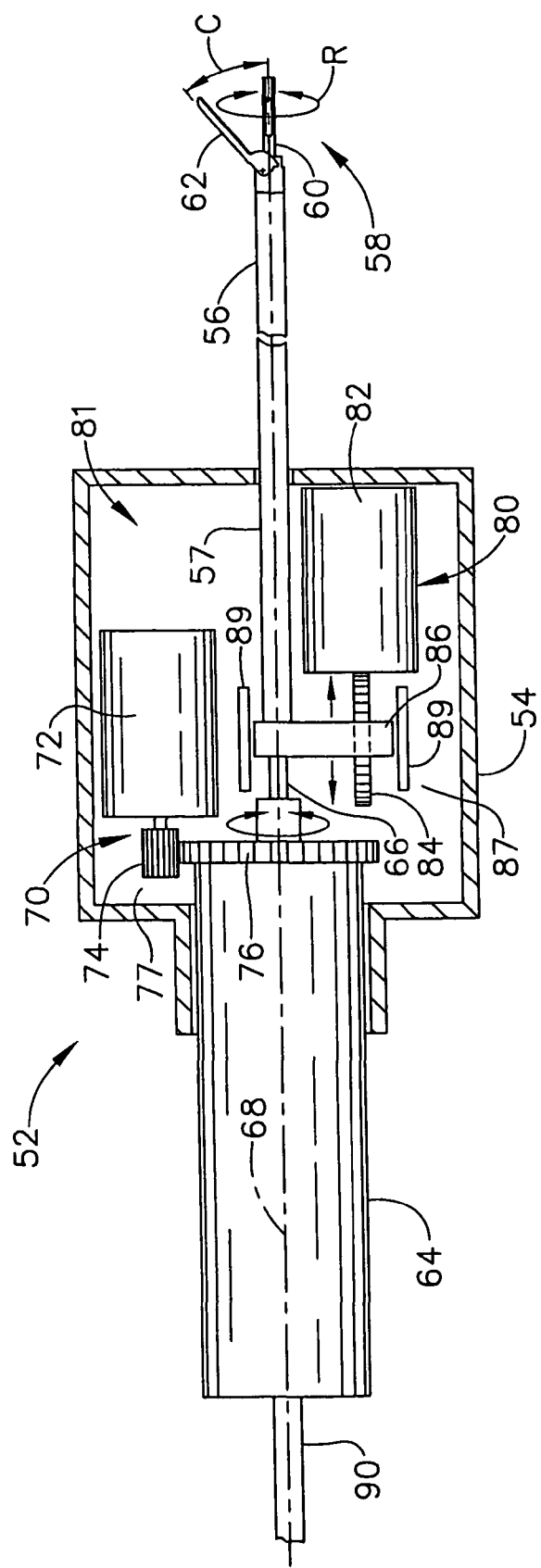
FIG. 3 is a cut-away top view of an ultrasonic surgical instrument according to one aspect, wherein the instrument includes a motorized actuating unit for operating an end effector.
Figure 4:
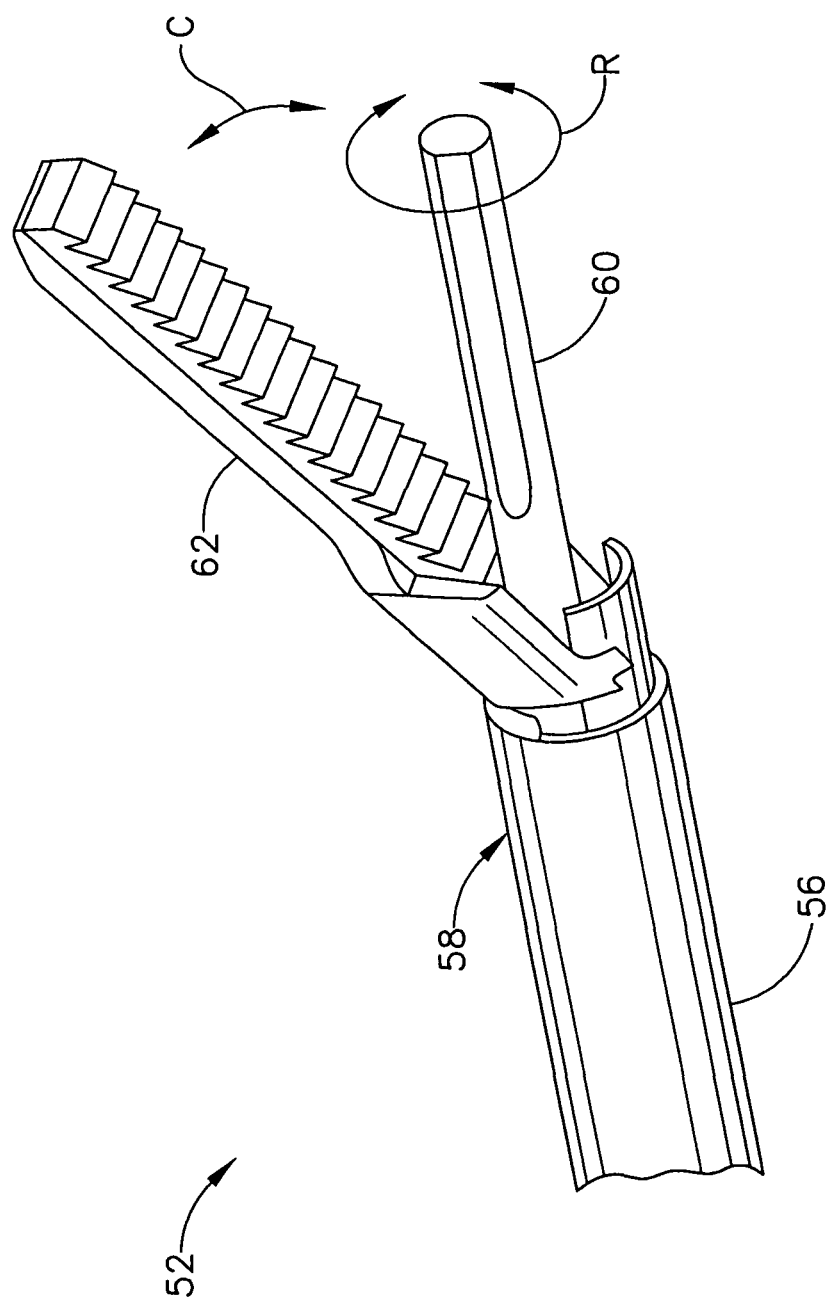
FIG. 4 is a perspective view of the distal portion of the ultrasonic surgical instrument shown in FIG. 3.

FIG. 3 is a cut-away top view of an ultrasonic surgical instrument 52 that may be held by a surgeon or releasably mounted to a movable arm of a robotic apparatus. Instrument 52 may include a base 54 and an elongate shaft 56 extending distally from the base 54. An end effector 58 on the distal end of shaft 56 may include a clamping element 62 (also referred to as a jaw) and an ultrasonic blade 60. FIG. 4 is a detailed, perspective view of end effector 58. Blade 60 is operatively connected by a waveguide 66 (FIG. 3) to an ultrasonic transducer 64 extending from the proximal end of base 54. Transducer 64, waveguide 66 and blade 60 may be similar in configuration and ultrasonic operation to the surgical ultrasonic transmission assemblies disclosed in the earlier referenced assemblies. Transducer 64 may be adapted to rotate about a central axis 68 with respect to base 54, such that blade 60 rotates about axis 68 with respect to clamping element 62, thereby allowing clamping element 62 to clamp against various surface portions of blade 60 for reasons to be described herein.

Instrument 52 may include an actuating unit 81 having a force transmission assembly 80 and a blade rotation assembly 70. Force transmission assembly 80 allows electrically controlled movement of clamping element 62 in a direction indicated by arrow "C". Blade rotation assembly 70 allows electrically controlled rotation of blade 60 about axis 68 in either direction as indicated by arrow "R". These movements may be directly controlled by the surgeon or automated as will be described herein.

In one aspect, force transmission assembly 80 may include a first electric motor 82 operatively connected to a remote control (not shown). Assembly 80 may include a first drive mechanism 87 that operatively engages motor 82 to an outer sheath 57 of shaft 56, such that electrical actuation of motor 82 moves outer sheath 57 in a distal or a proximal direction, depending on the rotational direction of motor 82. The distal end of outer sheath 56 may be operatively connected to clamping element 62, such that distal translation of sheath 57 moves clamping element 62 towards blade 60 and proximal translation of sheath 57 moves clamping element 62 away from blade 60. Drive mechanism 87 may include any one of a number of conventional mechanisms for converting the rotation of motor 82 to the translation of outer sheath 57. As shown in FIG. 3, drive mechanism 87 may include a lead screw 84 attached to motor 82 and operatively engaged with a follower 86 that is attached to the proximal end of outer sheath 57 and guided between tracks 89 formed on base 54.

Still referring to the aspect shown in FIG. 3, blade rotation assembly 70 may include a second electric motor 72 operatively connected to a remote control (not shown). Assembly 70 may include a second drive mechanism 77 operatively engaging motor 72 to ultrasonic transducer 64, such that electrical actuation of motor 72 causes transducer 64 to rotate in either direction about axis 68, thereby rotating waveguide 66 and blade 60 about axis 68. A power/control cable 90 extends proximally from transducer 64 and may be operatively connected to a user interface (not shown) as will be described. Second drive mechanism 77 may include any one of a number of conventional mechanisms for converting the rotation of motor 72 to the rotation of transducer 64. As shown in FIG. 3, drive mechanism 77 may include a pinion gear 74 attached to motor 72 and engaging a spur gear 76 attached to transducer 64. Motor 72 may be electrically actuated such that transducer 64 rotates +/−180 degrees about axis 68 as cable 90 flexibly twists in either direction.

First and second motors 72, 82 may be selected from a large number of commercially available DC servo-motors or other types of motors meeting numerous system requirements, including bidirectional shaft rotation, sufficient torque and rotational speed modulation, microprocessor control, size and cost.

As shown in FIG. 4, the distal portion of instrument 58 and the corresponding ultrasonic transmission assembly may be similar to that disclosed in U.S. Pat. No. 5,954,736 to Bishop et al. titled "Coagulator Apparatus Having Indexed Rotational Positioning," the entire contents of which are incorporated herein by reference. Instrument 58 may be ultrasonically driven by an ultrasonic generator (not shown) such as model number GEN04 available from Ethicon Endo-Surgery, Inc., Cincinnati, Ohio.

In another aspect of instrument 52, force transmission assembly 80 for the remote actuation of clamping element 62 may be provided by a gripper 82 of a surgical instrument 80 as disclosed in U.S. Pat. No. 6,783,524, beginning at col. 15, line 29.

Figure 5:
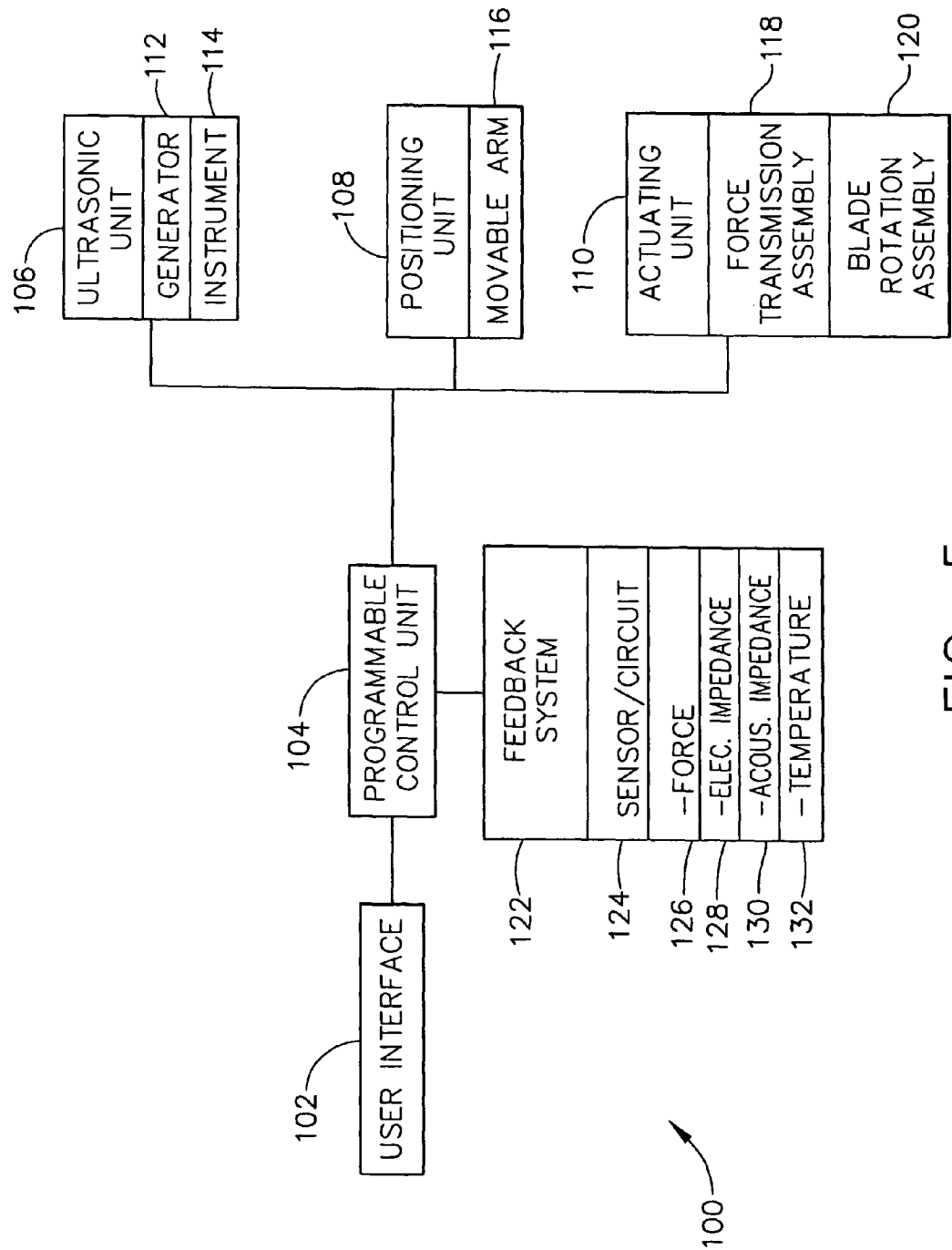
FIG. 5 is a block diagram showing an ultrasonic surgical system according to a first aspect, which is represented by solid-line blocks and according to a second aspect, which is represented by all the blocks.

Surgical instrument 52 and its various aspects may be included in an ultrasonic surgical system 100 shown in FIG. 5. System 100 may be used according to one or more automated surgical subroutines for the coordinated performance of a plurality of surgical tasks during a surgical procedure on a patient.

In FIG. 5, a first aspect of system 100 is represented by solid-line blocks and a second aspect is represented by all the blocks. A surgeon or operator may use system 100, for example, to automatically coagulate and cut tissue according to a predetermined surgical subroutine. All or parts of the surgical subroutine may be programmed by the operator into system 100 prior to the surgical procedure. Alternately, all or parts of the surgical subroutine may already be programmed into system 100.

System 100 generally may include a user interface 102, a programmable control unit 104, an ultrasonic unit 106, a positioning unit 108 and an actuating unit 110. Ultrasonic unit 106 may include an ultrasonic generator 112 and an ultrasonic surgical instrument 114. (In the following description of system 100, references to the end effector, the blade and the clamping element shall be applicable to end effector 58, blade 60 and clamping element 62 shown in FIG. 4, although many other types of ultrasonic end effectors may be adapted also for use with instrument 114.) Positioning unit 108 may include a movable arm 116 for positioning and orienting instrument 114 at a surgical site in the patient. Actuating unit 110 may include a force transmission assembly 118 for operating clamping element 60 on instrument 114 and a blade rotation assembly 120 for rotating an ultrasonic blade on instrument 114 about a central axis. System 100 may include or be used in conjunction with a robotic apparatus such as robotic apparatus 10 shown in FIG. 1. Alternatively, system 100 may be used without such a robotic apparatus, instead requiring the surgeon to hold and position the ultrasonic surgical instrument in a conventional manner and then initiating the automated surgical subroutine to perform certain surgical tasks.

User interface 102 may include a control box (not shown) having one or more controls for remotely operating instrument 114, a monitor (not shown) operatively connected to an endoscope or other type of image capture device for displaying an image of the surgical site and one or more controls for initiating and terminating an automated surgical subroutine that is programmed into control unit 104. User interface 102 may be located remotely or near the patient. Alternately, all or some of user interface 102 may be positioned on instrument 114 or other components of system 100.

Programmable control unit 104 may include a microprocessor programmable with at least one surgical subroutine for performing one or more surgical tasks simultaneously and/or in a coordinated manner. The subroutine may automatically control one or more surgical tasks, including movements of the blade, ultrasonic energization of the blade, actuation of the of the clamping element and responses to feedback signals. The duration of the subroutine is defined herein as an operative cycle, which may range, for example, from a fraction of a second to several seconds.

Control unit 104 may be provided with one or more surgical subroutines pre-programmed into the microprocessor, such that the surgeon may select and initiate a subroutine, for example, by actuating a control on user interface 102 prior to or during the surgical procedure. For example, the surgeon may specify that a blood vessel having a diameter of approximately 3 mm will be coagulated and cut. The subroutine would then automatically direct the instrument to provide a particular power level of ultrasonic energy for a particular period of time, to sweep the ultrasonic blade over the tissue and to actuate the clamping element according to a known effective treatment procedure. Alternately, control unit 104 may include any one of a number of conventional data input devices that would allow the surgeon to program the microprocessor prior to performing a surgical procedure. Such devices would allow inputting data using, for example, a floppy disk, a flash memory device or by keying in data when prompted by instructions from a programming software and displayed on the monitor.

Ultrasonic generator 112 of ultrasonic unit 106 may be a conventional ultrasonic generator such as the GEN04 (Ethicon Endo-Surgery, Inc.) generator. Instrument 114 may be operatively connected to generator 112 and releasably mounted to the movable arm 116 of positioning unit 108. Instrument 114 may be any one of the aspects of ultrasonic surgical instrument 30 shown in FIG. 2 and ultrasonic surgical instrument 52 shown in FIGS. 3 and 4, or equivalents thereof. A surgeon may operate user interface 102 to control movement of arm 116 in order to position the end effector of instrument 114 at the surgical site.

As previously noted, robotic apparatus 10 (FIG. 1) may be adapted for positioning instrument 114 and actuating the end effector of instrument 114. Control unit 104 may be operatively connected to apparatus 10 such that control unit 104 controls robotic apparatus 10 to move instrument 114 according to the surgical subroutine. For example, the subroutine may direct the movable arm of apparatus 10 to sweep the ultrasonic blade of instrument 114 laterally (side-to-side) and/or longitudinally while ultrasonic power is applied to the tissue in order to provide a larger hemostatic margin. Or the subroutine may direct apparatus 10 to reversibly actuate the clamping element on instrument 114 a number of times per second while the blade is ultrasonically energized in order to improve the quality of the tissue weld.

Positioning unit 108 may include other types of powered mechanisms for producing fine lateral and/or longitudinal movements of the ultrasonic blade and for actuating the clamping element of instrument 114 while the blade is ultrasonically energized. For example, various types of electric motors, electric solenoids, pneumatic actuators, hydraulic actuators, electrically actuated nickel/titanium shape-memory alloy mechanisms and other devices may be incorporated into instrument 114 and operatively connected to control unit 104 for positioning and actuating instrument 114 according to the surgical routine. In addition, instrument 114 may be handheld and positioning unit 108, rather than a robotic apparatus, may be a surgeon or other human operator.

Force transmission assembly 118 of actuating unit 110 actuates the clamping element of instrument 114 to apply a modulated force on tissue clamped against the ultrasonic blade according to the surgical subroutine. Force transmission assembly 118 may include force transmission components of movable arm 116 of positioning unit 108, wherein the force transmission components are mechanically coupled to instrument 114 for actuating the clamping element such as described in earlier referenced U.S. Pat. Nos. 6,783,524 and 6,352,532. The entire contents of U.S. Pat. No. 6,352,532 is incorporated herein by reference. Alternately, force transmission assembly 118 may include one or more components mounted, for example, inside of instrument 114 such as described for instrument 52 in FIG. 3.

Blade rotation assembly 120 may be similar to blade rotation assembly 80 shown in FIG. 3. Blade rotation assembly 120 rotates the ultrasonic blade about the central axis such that tissue may be clamped against various surface portions of the blade. For example, a first surface portion may be relatively flat for coagulating a broad area of tissue, whereas a second surface portion may have a relatively sharp edge for applying ultrasonic energy to a narrow region of tissue and cutting the tissue. The beginning of the surgical subroutine may direct the blade to present the first surface portion towards the tissue to create a wide region of coagulated tissue on a blood vessel, for example, and the ending of the surgical subroutine may direct the blade to present the second surface portion towards the tissue to cut through the center of the wide coagulated region.

In addition to electric motor actuators, other types of actuators that may be adapted for use in force transmission assembly 118 and in blade rotation assembly 120 include, for example, electromagnetic coil actuators, hydraulic actuators and pneumatic actuators.

A second aspect of an ultrasonic surgical system 100, represented by the blocks in FIG. 5, includes the elements of the first aspect and, in addition, a feedback system 122. Feedback system 122 may include at least one sensor 122 for measuring an operational parameter associated with the operational performance of the ultrasonic surgical system during the operative cycle.

In one aspect, feedback system 122 may include a force sensor 126 that measures the mechanical clamping force of the clamping element. Force sensor 126 may be any one of a number of force sensors well-known in the art, including a strain gauge or a piezoelectric sensor mounted on the clamping element on a force-transmitting component (not shown) of force transmission assembly 118. Force sensor 126 may be electrically connected to control unit 104, which may process a feedback signal from force sensor 126 during the operative cycle. Control unit 104 may then augment the ultrasonic power level, clamping force and/or blade movements according to the surgical subroutine and based on the force feedback. Control unit 104 may also halt the surgical subroutine if a predetermined force is exceeded in order to prevent injury to the patient or damage to instrument 114.

Force sensor 126 may enable control unit 104 to command actuating unit 110 to supply any one of a plurality of clamping force-versus-time profiles to tissue held between the clamping element and the blade. For example, the surgical subroutine may command the actuation of the clamping element to provide a particular discrete force during one or more portions of the operative cycle. The discrete force may be pulsed or applied repetitively at a frequency of about 1-10 Hertz in one aspect, for example. Alternately, the surgical subroutine may direct the actuation of the clamping element to provide an ascending and/or descending ramped force profile or a parabolic force profile during the operative cycle, for example. Alternately, a relatively light force may be applied while the blade sweeps through a treatment region on the tissue and/or rotates about the central axis during coagulation of the tissue. Then, a relatively high force may be applied in order to cut the tissue in the middle of the treatment region.

In another aspect, feedback system 122 may include an electrical impedance measuring circuit 128 for measuring the electrical impedance of the tissue being treated by the end effector during the operation cycle. Because electrical impedance of living tissue typically increases as the tissue is coagulated, measurement of electrical current through the tissue as it is being ultrasonically treated provides an indication of the level of coagulation. The clamping element and blade, both being electrical conductors, may be electrically connected to an impedance measuring circuit such that current passing through the tissue that is clamped between the clamping element and the blade may be monitored by control unit 104. In one aspect, the surgical subroutine may be programmed, for example, so that when electrical impedance reaches a predetermined magnitude, the ultrasonic power is turned off and the subroutine is halted.

In another aspect, feedback system 122 may include an acoustical impedance measuring circuit 130, such as is well-known in the art, for measuring acoustical impedance of the tissue being ultrasonically treated. Acoustical impedance may be characterized as the ability of a material to conduct a sound wave. Generally, as acoustical impedance increases, the speed of sound through the material decreases. As tissue is coagulated, tissue elasticity decreases and tissue density increases, thereby decreasing acoustical impedance. Acoustical impedance measuring circuit 130 may be physically located inside of generator 112 of ultrasonic unit 106. Control unit 104 may process a feedback signal from circuit 130 and modify or halt the surgical subroutine based on the acoustical feedback.

In yet another aspect, feedback system 122 may include a temperature sensor 132 and a temperature measuring circuit (not shown). Temperature sensor 132 may be mounted on or near the end effector of instrument 114 in order to measure the temperature of the blade or clamping element, the treated tissue, an object near the treated tissue or a fluid surrounding the treated tissue. Temperature sensor 132 may be a thermocouple, a thermistor, an infrared temperature sensor or any one of a number of other temperature sensors well known in the art. Temperature feedback signals may be transmitted to control unit 104, which may process the signal to modify or halt the surgical subroutine.

Any combination of the aforementioned aspects of feedback system 122 may be included in ultrasonic surgical system 100 to transmit feedback signals to control unit 104, so that control unit 104 may process the signals during the operative cycle and respond according to the surgical subroutine.

Figure 6:
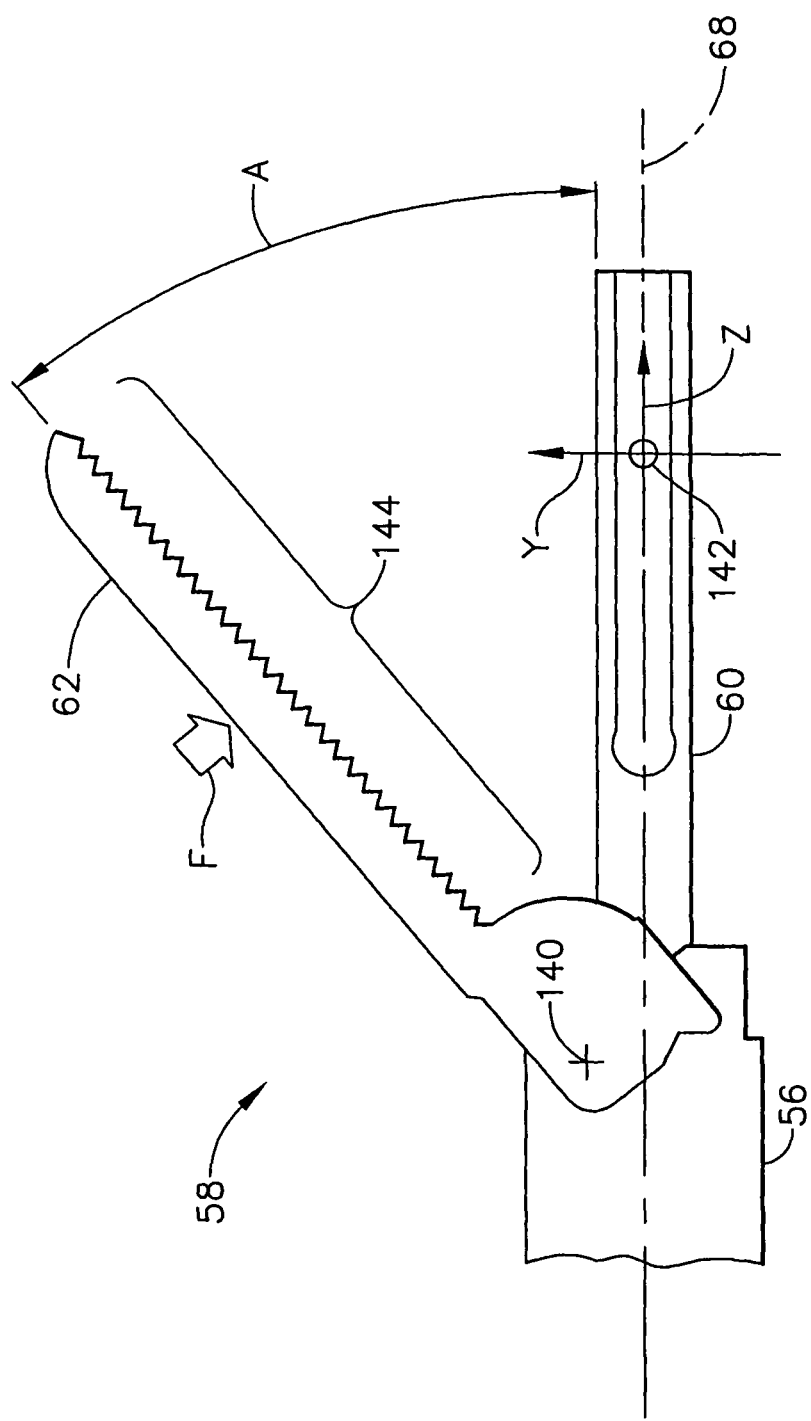
FIG. 6 is a side view of the distal portion of the instrument shown in FIG. 4.

FIGS. 6-8 illustrate examples of end effector movements that may be automated while the blade if instrument 114 is ultrasonically energized according to the surgical subroutine. These movements may include clamping element angle adjustment, lateral positioning of the end effector in the x-axis direction, longitudinal positioning of the end effector in the z-axis direction, and blade rotation about the z-axis. The lateral and longitudinal positioning of the end effector are also referred to as "sweeping." These movements will be defined herein as they may pertain to end effector 58 shown in FIG. 4, but they are also applicable to other ultrasonic end effectors having a blade and a clamping element. For end effectors having only a blade and without a clamping element, the movements of blade rotation and clamping element angle adjustment are excluded.

FIG. 6 is a side view of the distal portion of instrument 52 in FIG. 4 and shows the y-axis and the z-axis of the ordinate system positioned on an origin 142. Central axis 68 extends through shaft 56 and lies along the z-axis. Clamping element 62 pivotally attaches to shaft 56 at a pivot 140 and may be positioned at a clamping element angle "A" with respected to blade 60. Clamping element angle A may be remotely adjustable, for example, to vary approximately in the range of zero to 60 degrees by partial actuation of clamping element 62. When clamping element 62 is actuated to move in a closing direction towards blade 60, clamping element 62 clamps onto tissue positioned between a serrated portion 144 and blade 60 with an average clamping force "F" perpendicular to clamping element 62 and near the center of serrated portion 144. When clamping element angle A is approximately zero such as when clamping thin tissue, the average clamping force F is approximately directed through origin 142.

FIG. 7 is a top view of the distal portion of instrument 52 shown in FIG. 2 and shows origin 142, the z-axis and the x-axis of the ordinate system. In certain situations, a surgeon may prefer to treat a broad area of tissue in order, for example, to provide safe margins of coagulated tissue for proper hemostasis. The surgeon may ultrasonically treat tissue in a treatment region 146 (also referred to as a central treatment region) defined in the lateral direction of the x-axis by "+DX" and "−DX" and in the longitudinal direction of the z-axis by "+DZ" and "−DZ" about origin 142.

End effector 58 may be swept laterally and/or longitudinally within treatment region 146 while blade 60 is ultrasonically energized at a low power level and clamping element angle A is held at a desired opening. Alternately, blade 60 may be energized at a high power level while clamping element angle A is near zero and a high clamping force is applied to the tissue. Clamping force may also be applied repeatedly, such as in a rapid-pulsed fashion, as blade 60 is energized, in order to agitate and to circulate tissue fluids in the vicinity of the energy application. As those skilled in the art may appreciate, there are many different combinations of clamping, energizing and sweeping that may be used to treat various kinds of tissue in the many different kinds of surgical situations.

FIG. 8 is a cross-sectional view taken at line 8-8 in FIG. 7 of end effector 58 when clamping element angle A is zero. Blade 60 may include a first surface 148, a second surface 150, a third surface 152, a fourth surface 154 and a fifth surface 156, together defining a blade profile 15. FIG. 5 shows an aspect of blade profile 160 that may be particularly useful, for example, for transecting the cystic duct of the gall bladder during a cholecystectomy. Blade profile 160 may have many other geometrical shapes depending on the surgical application and other requirements of the instrument.

Referring to FIGS. 6 and 8, blade 14 is rotatable about the z-axis so that any one of surfaces 148, 150, 152, 154, 156 or an edge between the surfaces may interface with clamping element 62 while tissue is held therebetween. Blade 60 may be rotated in a positive direction "+RZ" and a negative direction "−RZ" about the z-axis. For example, blade 60 may be rotated so that an edge 158 engages tissue when a high concentration of force on the tissue is desired, such as during cutting. Alternately, blade 60 may be rotated so that surface 148 engages tissue when it is desired to distribute clamping force over a wide area such as during coagulating. Or blade 60 may be rotated back and forth within an angular range as surface 150 engages tissue, to produce a "rolling" effect as blade 60 is ultrasonically energized. As apparent to those skilled in the art, many different combinations of rotating and energizing blade 60 may be devised to rapidly and hemostatically cut and/or coagulate various types of tissue for many different surgical situations.

Control unit 104 may be programmed to direct the fine movement of instrument 114 along a predetermined path as blade 60 is energized and clamping force is applied, according to the surgical subroutine, in order to accelerate and/or enhance tissue treatment within the tissue treatment region 146 (FIG. 7). The predetermined path may include any combination of lateral sweeping in the x-direction, longitudinal sweeping in the y-direction and blade rotation about the z-axis. FIGS. 9 through 17 are graphs that illustrate the operation of control system 100 according to an exemplary surgical subroutine during an operative cycle in which a surgical procedure is performed on tissue. The graphs are shown without actual values and are intended to illustrate relative parametric magnitudes and timing of the concurrent surgical tasks. The total time represented on the graphs may be, for example, approximately in the range of 2 to 10 seconds. Many other surgical subroutines are possible and may be devised according to the envisioned surgical situations and programmed into control unit 104.

The graph shown in FIG. 9 and again in FIG. 14 illustrates an ultrasonic power-versus-time profile, showing ultrasonic "U/S" power (watts) versus time "T" (seconds) for the operative cycle. Ultrasonic power is a function of ultrasonic frequency and amplitude. The ultrasonic power transmitted to tissue may be effectively controlled, therefore, by variation of ultrasonic frequency and amplitude, and by selection of the clamping force (pressure) applied to the tissue. The ultrasonic power may be applied intermittently as shown to coagulate tissue between each repositioning of the end effectors, and to cut the tissue, during which the ultrasonic power may reach a maximum value, for example, of approximately twenty watts.

Figure 9:
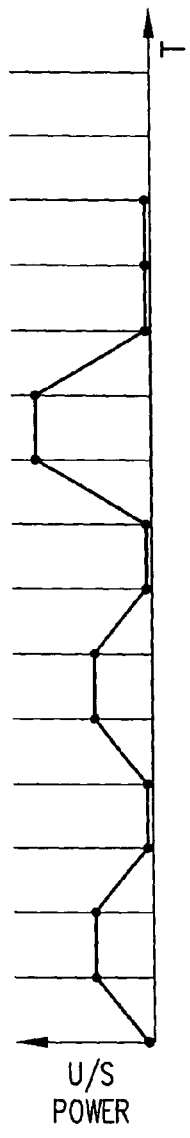
FIG. 9 is a graph depicting an ultrasonic power applied to an ultrasonic end effector versus time during an exemplary operative cycle in accordance with one aspect of the ultrasonic surgical system.
Figure 10:
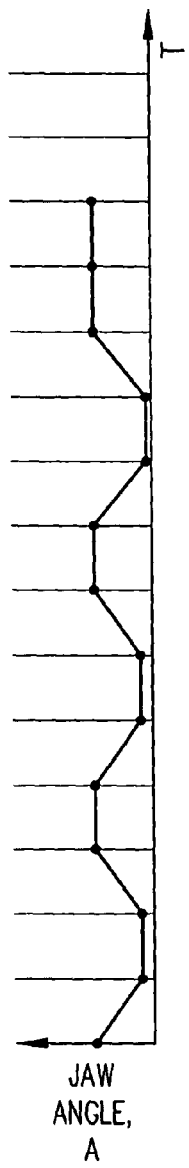
FIG. 10 is a graph depicting a clamping element angle of the end effector versus time during the operative cycle in accordance with one aspect of the ultrasonic surgical system.

FIG. 10 illustrates a clamping element angle-versus-time profile for the same operative cycle as illustrated in FIG. 9. As the ultrasonic power is applied, the clamping element angle A may vary with time as shown, indicating how ultrasonic power may only be applied when a clamping force is applied to the tissue, as described in FIG. 6.

Figure 11:
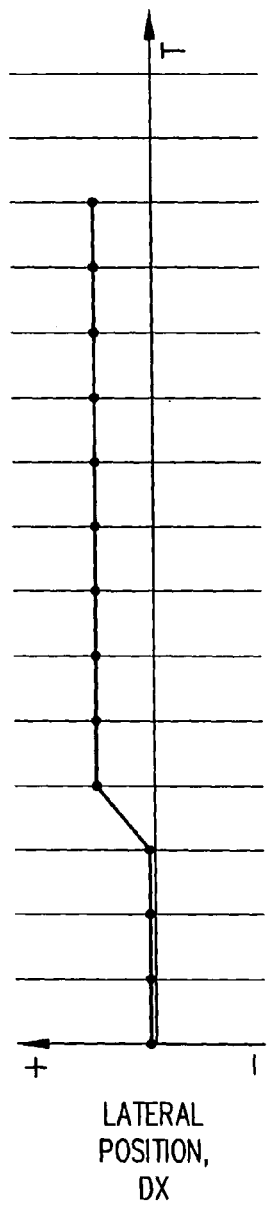
FIG. 11 is a graph depicting a lateral position of the end effector versus time during the operative cycle in accordance with one aspect of the ultrasonic surgical system.

FIGS. 11 and 12 show graphs that illustrate how the surgical subroutine may concurrently direct the fine movement of the end effectors in the x-axis direction (lateral position, DX) and the z-axis direction (longitudinal position, DZ), as described for FIG. 7. FIG. 11 illustrates a lateral position-versus-time profile and FIG. 12 illustrates a longitudinal position-versus-time profile for the same operative cycle shown in FIG. 9.

FIG. 13 shows a graph that illustrates a blade rotation-versus-time profile for the same operative cycle shown in FIG. 9. Commands dictated by the surgical subroutine direct the rotation of blade 60 about the z-axis (blade rotation, RZ), as described for FIG. 8.

FIGS. 15, 16 and 17 are graphs showing exemplary feedback signals provided by feedback system 122 of control system 60 (FIG. 5), measured concurrently during the operative cycle shown in FIG. 14. As noted previously, control unit 104 may process the feedback signals and respond according to the surgical subroutine.

According to one aspect, a method for ultrasonically treating the tissue of a surgical patient may include providing the ultrasonic surgical system according to the first aspect described in FIG. 5, programming the control unit with a surgical subroutine for performing a plurality of surgical tasks, positioning the end effector of the instrument at a surgical site inside a body cavity of the patient and initiating the surgical subroutine of the control unit, whereby the system automatically performs the surgical tasks according to the surgical subroutine.

The surgical tasks of the method may be defined to include energizing the end effector according to an ultrasonic power level profile of the surgical subroutine during the operative cycle and one or both of the following: sweeping the ultrasonic end effector against the tissue in a lateral direction within a treatment region according to a lateral sweep profile of the surgical subroutine during the operative cycle; sweeping the ultrasonic end effector against the tissue in a longitudinal direction within a treatment region according to a longitudinal sweep profile of the surgical subroutine during the operative cycle.

The ultrasonic surgical system provided in the method may further include a clamping element, an ultrasonic blade and an actuating unit having a force transmission assembly operatively connected to the clamping element and to the control unit such that the force transmission assembly may be actuated to operate the clamping element to apply a variable clamping force to tissue held between the clamping element and the blade. The surgical tasks, therefore, may be defined to include operating the clamping element to apply a variable clamping force to tissue held between the clamping element and the blade according to a clamping force profile of the surgical subroutine during the operative cycle.

The ultrasonic surgical system provided in the method may further include the end effector having an ultrasonic blade and an actuating unit having a blade rotation assembly operatively connected to the blade and to the control unit such that the blade rotation assembly may be actuated to rotate the blade about a central axis. The surgical tasks, therefore, may be defined to include rotating the blade about the central axis according to a blade rotation profile of the surgical subroutine during the operative cycle.

In another aspect, a method for ultrasonically treating the tissue of a surgical patient may include providing the ultrasonic surgical system according to the second aspect described in FIG. 5, wherein the system further includes a feedback system having at least one sensor positioned in at least one of the ultrasonic and positioning units and having an associated sensor circuit, wherein the feedback system is operatively connected to the control unit, and wherein a feedback signal associated with an operational performance parameter of the instrument during the operative cycle may be transmitted from the sensor to the control unit such that the control system can process the feedback signal and respond according to the surgical subroutine. The method may further include programming the control unit with a surgical subroutine for performing a plurality of surgical tasks, positioning the end effector of the instrument at a surgical site inside a body cavity of the patient and initiating the surgical subroutine of the control unit, whereby the system automatically performs the surgical tasks, processes the feedback signal and responds to the feedback signal according to the surgical subroutine.

Although various aspects of an ultrasonic surgical system and method have been shown and described, it should be understood that modifications may occur to those skilled in the art. The present application contemplates and includes such modifications and is limited only by the scope of the claims.

What is claimed is:

1. An ultrasonic surgical system comprising:
   an ultrasonic unit including an instrument operatively connected to an ultrasonic generator, wherein said instrument includes an end effector having a clamping element and an ultrasonic blade;
   a positioning unit including a movable arm, wherein said moveable arm is adapted to hold said instrument of said ultrasonic unit;
   a control unit in communication with said ultrasonic unit and said positioning unit, said control unit being programmed with a surgical subroutine for performing a plurality of surgical tasks in an operative cycle, wherein at least one surgical task of said plurality includes reversibly and repeatedly actuating said clamping element to apply a modulated clamping force to tissue clamped against said ultrasonic blade; and
   a user interface in communication with said control unit, said user interface being configured to initiate said operative cycle of said surgical subroutine such that said plurality of surgical tasks are automatically performed during said operative cycle.

2. The ultrasonic surgical system of claim 1 wherein said plurality of surgical tasks include energizing said ultrasonic blade according to an ultrasonic power-level-versus-time profile of said surgical subroutine.

3. The ultrasonic surgical system of claim 2 wherein said plurality of surgical tasks include sweeping said ultrasonic blade against body tissue clamped against said ultrasonic blade, while said ultrasonic blade is energized, according to a position-versus-time profile of said surgical subroutine.

4. The ultrasonic surgical system of claim 2 wherein said plurality of surgical tasks include sweeping said ultrasonic blade against body tissue clamped against said ultrasonic blade, while said ultrasonic blade is energized, in a lateral direction within a treatment region, and according to a lateral sweep profile of said surgical subroutine.

5. The ultrasonic surgical system of claim 1 further comprising an actuating unit having a force transmission assembly operatively connected to said clamping element and in communication with said control unit, wherein said force transmission assembly is adapted to actuate said clamping element and apply a variable clamping force to body tissue clamped against the ultrasonic blade.

6. The ultrasonic surgical system of claim 5 further comprising a feedback system including a force sensor mounted on said clamping element or a force-transmitting component of said force transmission assembly, wherein said feedback system is operatively connected to said control unit, and wherein a feedback signal is transmitted from said force sensor to said control unit such that said control unit processes said feedback signal and responsively varies clamping force according to a clamping force-versus-time profile of said surgical subroutine.

7. The ultrasonic surgical system of claim 1 further comprising an actuating unit having a blade rotation assembly operatively connected to said ultrasonic blade and in communication with said control unit, wherein said blade rotation assembly may be actuated to rotate said ultrasonic blade about a central axis independently of any rotation of said clamp element, and wherein said plurality of surgical tasks include rotating said ultrasonic blade about said central axis according to a blade rotation-versus-time profile of said surgical subroutine.

8. The ultrasonic surgical instrument of claim 7 wherein said ultrasonic blade includes a plurality of blade surface portions arranged around said central axis and defining a blade cross-sectional profile, and wherein said ultrasonic blade is rotated such that any one of said surface portions may interface with said clamping element.

9. The ultrasonic surgical system of claim 8 wherein said blade surface portions include at least one of a relatively flat surface portion, a relatively rounded surface portion, a relatively narrow surface portion and an edge surface portion.

10. The ultrasonic surgical system of claim 1 wherein said positioning unit is a surgical robotic apparatus having a work station in communication with said movable arm.

11. The ultrasonic surgical system of claim 1 wherein said at least one surgical task reversibly and repeatedly actuates the clamping element to apply a modulated, tissue-welding clamping force at a predetermined number of times per second.

12. The ultrasonic surgical system of claim 1 wherein said at least one surgical task reversibly and repeatedly actuates the clamping element according to a clamping element angle-versus time profile during said operative cycle.

13. An ultrasonic surgical system comprising:
   an ultrasonic unit including an instrument operatively connected to an ultrasonic generator, wherein said instrument has an ultrasonic end effector positioned on a distal end of a shaft and an actuating unit, said ultrasonic end effector including a clamping element and an ultrasonic blade, and said actuating unit including a force transmission assembly adapted to actuate said clamping element;

a control unit operatively connected to said actuating unit of said ultrasonic unit, wherein said control unit is programmed with a surgical subroutine for performing a plurality of surgical tasks in an operative cycle, wherein at least one surgical task of said plurality includes reversibly and repeatedly actuating said clamping element to apply a modulated clamping force to tissue clamped against said ultrasonic blade; and a user interface operatively connected to said control unit for initiating said operative cycle of said surgical subroutine such that said plurality of surgical tasks are automatically performed during said operative cycle.

14. The ultrasonic surgical system of claim 13 wherein said at least one surgical task reversibly and repeatedly actuates the clamping element to apply a modulated, tissue-welding clamping force at a predetermined number of times per second.

15. The ultrasonic surgical system of claim 13 wherein said at least one surgical task reversibly and repeatedly actuates the clamping element according to a clamping element angle-versus time profile during said operative cycle.

16. The ultrasonic surgical system of claim 13 wherein said force transmission assembly is adapted to actuate said clamping element and apply a variable clamping force to body tissue clamped against the ultrasonic blade.

17. The ultrasonic surgical system of claim 16 further comprising a feedback system including a force sensor mounted on said clamping element or a force-transmitting component of said force transmission assembly, wherein said feedback system is operatively connected to said control unit, and wherein a feedback signal is transmitted from said force sensor to said control unit such that said control unit processes said feedback signal and responsively varies clamping force according to a clamping force-versus-time profile of said surgical subroutine.

18. A method for ultrasonically treating a tissue of a patient, said method comprising:

providing an ultrasonic surgical system comprising an ultrasonic unit including an instrument operatively connected to an ultrasonic generator, wherein said instrument includes an end effector having a clamping element and an ultrasonic blade, a control unit in communication with said ultrasonic unit, and a user interface in communication with said control unit;

programming said control unit with a surgical subroutine for performing a plurality of surgical tasks, wherein at least one surgical task of said plurality includes reversibly and repeatedly actuating said clamping element to apply a modulated clamping force to tissue clamped against said ultrasonic blade;

positioning said end effector of said instrument at a surgical site inside a body cavity of said patient with tissue disposed between said clamping element and said ultrasonic blade; and initiating said surgical subroutine such that said ultrasonic surgical system automatically performs said plurality of surgical tasks according to said surgical subroutine.

19. The method of claim 18 wherein said plurality of surgical tasks include energizing said ultrasonic blade according to an ultrasonic power-level-versus-time profile of said surgical subroutine.

* * * * *